United States Patent [19]

Gravestock

[11] Patent Number: 4,503,062

[45] Date of Patent: Mar. 5, 1985

[54] AZOLYL:SUBSTITUTED ALICYCLIC ALCOHOLS

[75] Inventor: Michael B. Gravestock, Cheadle, England

[73] Assignee: Imperial Chemical Industries PLC, London, England

[21] Appl. No.: 479,914

[22] Filed: Mar. 28, 1983

[30] Foreign Application Priority Data

Apr. 22, 1982 [GB] United Kingdom ............... 8211705

[51] Int. Cl.$^3$ .................... A01N 43/50; A01N 43/64; C07D 233/60; C07D 249/08
[52] U.S. Cl. .................... 514/383; 514/399; 548/262; 548/336; 548/346; 549/349; 549/365; 549/435; 549/437; 549/546; 568/812
[58] Field of Search .................... 548/336, 346, 262; 424/269, 273 R

[56] References Cited

U.S. PATENT DOCUMENTS

| | | | |
|---|---|---|---|
| 3,636,002 | 1/1972 | Godefroi et al. | 548/346 |
| 4,289,526 | 9/1981 | Worthington et al. | 548/262 |
| 4,414,210 | 11/1983 | Miller et al. | 568/645 |

FOREIGN PATENT DOCUMENTS

| | | | |
|---|---|---|---|
| 52425 | 5/1982 | European Pat. Off. | 548/262 |
| 2654890 | 6/1977 | Fed. Rep. of Germany | 548/262 |
| 1464224 | 2/1977 | United Kingdom | 548/262 |

*Primary Examiner*—Alton D. Rollins
*Attorney, Agent, or Firm*—Cushman, Darby & Cushman

[57] ABSTRACT

This invention relates to novel alicyclic alcohol compounds of the formula

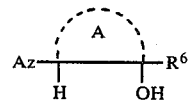

wherein Az is imidazole or 1,2,4-triazole, $R^6$ is optionally substituted phenyl and A is an alicyclic ring optionally benzo-fused, which compounds possess pharmaceutical, veterinary, agricultural and horticultural antifungal properties; together with a process for their manufacture, compositions containing them, and a method of combatting plant fungal diseases.

10 Claims, No Drawings

AZOLYL:SUBSTITUTED ALICYCLIC ALCOHOLS

This invention relates to novel alicyclic alcohol compounds which are useful as antifungals, to processes for their manufacture, to antifungal compositions containing them, and to a method of using them for combatting fungal infections of plants. The antifungal compositions may be in a form suitable for oral or topical administration to human or other animals for the treatment of fungus diseases, especially candidosis and human dermatophyte infections, or they may be in a form suitable for administration to plants or seeds, or to the surrounding environment thereof.

Triazole and imidazole compounds of various types are known to possess antifungal properties. For example, European Specification Number 11768 discloses triazole compounds of the formula:

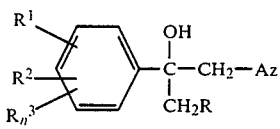

in which Az is a triazolyl radical, R is an optionally substituted phenyl, naphthyl or tetrahydronaphthyl radical, $R^1$ is an optionally substituted phenyl or cycloalkyl radical, $R^2$ is hydrogen or $R^1$ and $R^2$ are in an ortho-relationship and form an optionally substituted polymethylene bridge or together with the phenyl ring form naphthyl, $R^3$ is halogen or an alkyl, alkoxy or halogenoalkyl radical, and n is 0, 1, 2 or 3;

European Specification Number 11769 discloses similar compounds in which the substituent $-CH_2R$ is replaced by an optionally substituted phenyl, naphthyl or tetrahydronaphthyl radical;

and our European Specification Number 15756 discloses compound of the formula:

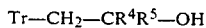

wherein Tr is a 1,2,4-triazolyl radical, $R^4$ is an alkyl, cycloalkyl or optionally substituted phenyl radical, and $R^5$ is an optionally substituted phenyl or optionally substituted benzyl radical.

The present invention concerns compounds in which a triazole or imidazole ring, a hydroxy radical and a phenyl radical are substituents in an alicyclic ring system.

Thus, according to this present invention, there is provided an alicyclic alcohol compound of the formula:

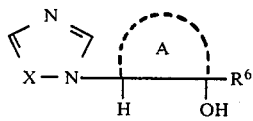

wherein $R^6$ is an unsubstituted phenyl radical, or a phenyl radical bearing 1 to 5 substituents selected from halogen atoms, amino, nitro, cyano, phenyl and halogenophenyl radicals, and alkyl, halogenoalkyl, alkoxy, halogenoalkoxy, alkylthio, alkylenedioxy, alkylamino, and dialkylamino radicals, wherein each alkyl, alkoxy or alkylene part is of 1 to 10 carbon atoms, X is a nitrilo or methine radical, and the ring A is a cyclopentane, cyclohexane or cycloheptane ring, or an indane, tetrahydronapthalene or benzocycloheptane ring each of which is either unsubstituted, or is substituted in the benzene ring thereof with 1 to 4 substituents as defined above.

Preferred compounds of the invention are those wherein the ring A is a cyclohexane, or an optionally substituted indane or 1,2,3,4-tetrahydronaphthyl ring.

The phenyl ring $R^6$ and the benzene ring in ring system A, if present, are preferably unsubstituted or bear only one or two substituents. Preferred such substituents are halogen atoms, particularly chlorine and fluorine atoms.

Particular values for $R^6$ are therefore, for example, 2-, 3- or 4-chlorophenyl, 2-, 3- or 4-fluorophenyl, 2-, 3- or 4-bromophenyl, 2,3-, 2,4-, 2,5-, 2,6-, 3,4- or 3,5-dichlorophenyl, 2,3-, 2,4-, 2,5-, 2,6-, 3,4- or 3,5-difluorophenyl, 2-chloro-4-fluorophenyl, 4-chloro-2-fluorophenyl, 2-bromo-4-chlorophenyl and 4-bromo-2-chlorophenyl radicals, and of these the 4-chlorophenyl, 4-fluorophenyl, 2,4-dichlorophenyl and 2,4-difluorophenyl radicals are preferred.

Particular values for the ring system A are cyclohexane, indane, 4-, 5-, 6- and 7-chloroindane, 4-, 5-, 6- and 7-fluoroindane, 4,5-, 5,6-, 6,7-, 4,6-, 4,7- and 5,7-dichloroindane, 4,5-, 5,6-, 6,7-, 4,6-, 4,7- and 5,7-difluoroindane, 1,2,3,4-tetrahydronaphthalene, 5-, 6-, 7- and 8-chloro-1,2,3,4-tetrahydronaphthalene, 5-, 6-, 7- and 8-fluoro-1,2,3,4-tetrahydronaphthalene, 5,6-, 5,7-, 5,8-, 6,7-, 6,8- and 7,8-dichloro-1,2,3,4-tetrahydronaphthalene and 5,6-, 5,7-, 5,8-, 6,7-, 6,8- and 7,8-difluoro-1,2,3,4-tetrahydronaphthalene, and of these, indane, 5-chloro-, 6-chloro-, 6,7-dichloro- and 6-fluoro-1,2,3,4-tetrahydronaphthalene are preferred.

Similarly, a preferred halogen in a halogenoalkyl or halogenophenyl substituent in $R^6$ is a chlorine or fluorine atom.

Preferred alkyl, halogenoalkyl, alkoxy, halogenoalkoxy, alkylthio, alkylenedioxy and alkylamino substituents in $R^6$ contain from 1 to 6 carbon atoms and especially 1 to 3 carbon atoms. Similarly, preferred dialkylamino substituents in $R^6$ contain 1 to 6 carbon atoms and especially 1 to 3 carbon atoms, in each of the alkyl radicals thereof.

Particular such substituted phenyl radicals are therefore, for example, amino, nitro, cyano, methyl, ethyl, propyl, butyl, pentyl, hexyl, heptyl, octyl, nonyl, decyl, chloromethyl, dichloromethyl, trichloromethyl, fluoromethyl, difluoromethyl, trifluoromethyl, 2,2,2-trichloroethyl, 2,2,2-trifluoroethyl, methylthio, ethylthio, propylthio, hexylthio, decylthio, methylenedioxy, ethylidenedioxy, 1-methylethylidenedioxy, 1,2-ethylenedioxy, 1,2-propylenedioxy, 1-methyl-1,2-propylenedioxy, 1,2-butylenedioxy, 1-methyl-1,2-butylenedioxy, 1-ethyl-1,2-butylenedioxy, methoxy, ethoxy, propoxy, hexyloxy, decyloxy, chloromethoxy, trichloromethoxy, fluoromethoxy, 2,2,2-trichloroethoxy, methylamino, ethylamino, propylamino, hexylamino, decylamino, dimethylamino, diethylamino, ethylmethylamino, dipropylamino, dihexylamino and didecylamino substituted phenyl radicals.

A preferred value for X is a nitrilo radical.

A particularly preferred group of compounds of the formula I comprises those compounds wherein X is a nitrilo radical, A is a 1,2,3,4-tetrahydronaphthalene ring and the $R^6$ and hydroxy substituents are on C-1 of the tetrahydronaphthalene ring.

Particular preferred compounds within this preferred group are 1-(4-chlorophenyl)-1,2,3,4-tetrahydro-2-(1,2,4-triazol-1-yl)-1-naphthol and 6-chloro-1-(4-chlorophenyl)-1,2,3,4-tetrahydro-2-(1,2,4-triazol-1-yl)-1-naphthol.

It will be appreciated that, in compounds of the formula I, there are two asymmetric carbon atoms, namely the carbon atom in ring A to which $R^6$ and the hydroxy group are attached, and the carbon atom in ring A to which the triazole or imidazole ring and a hydrogen atom are attached. It is therefore apparent that such compounds may exist in racemic form or in one of four optically active forms. It is common general knowledge how such racemic compounds may be obtained as their optical isomers, and how the respective fungicidal properties of the separate optical isomers may be determined.

The compounds of the formula I may be manufactured by any of the conventional processes known in the chemical literature for the manufacture of analogous compounds. Thus, the following process is provided as a further feature of this invention:

the reaction of a compound of the formula:

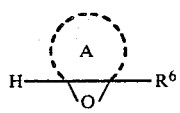
II or

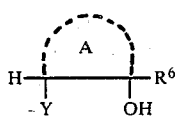
III wherein A and $R^6$ have the meanings stated above, and Y is a bromine or chlorine atom, with imidazole or 1,2,4-triazole, either in the presence of an acid-binding agent, or in the form of one of its alkali metal salts in an inert solvent.

A suitable alkali metal salt of imidazole or 1,2,4-triazole is, for example, the sodium or potassium salt, and a convenient solvent is, for example, dimethylformamide, dimethylacetamide, methanol, ethanol or acetonitrile, at a temperature in the range 20°-100° C.

The starting material of the formula II may be obtained by reacting a ketone of the formula IV with a Grignard reagent, $R^6$MgHalogen, to give a tertiary alcohol V, which is dehydrated to an olefin VI, and the double bond of the olefin VI is epoxidised, for example with a peroxycarboxylic acid such as m-chloroperbenzoic acid, to the required epoxide starting material II.

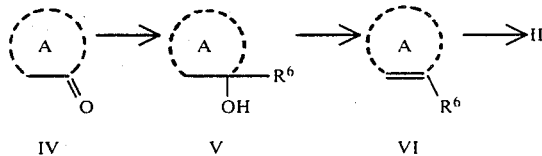

IV     V     VI

The starting material of the formula III may be obtained by the reaction of an olefin VI with, for example, N-bromoacetamide in aqueous acetone at 10°-25° C. for a few hours.

As indicated above, the compounds of the invention possess antifungal properties which are useful in the treatment of candidosis and human dermatophyte infections.

This antifungal activity against Candida albicans, a causative fungus of candidosis, and Trichophyton mentagrophytes, var. quinkeanum, a causative fungus or ringworm, was demonstrated as follows:

Female mice of around 30 g. weight are injected sub-cutaneously on a Friday with 0.5 mg. of oestradiol benzoate. The following Monday (day 0) they are clipped on the back and then dosed orally with test compounds. They are then inoculated with Candida albicans in the vagina and Trichophyton mentagrophytes var. quinkeanum on the back, and then given a second dose of the same compound. Dosing is repeated once daily on days 1-4. On day 7 skin lesions are scored visually and vaginal samples taken for culture on agar. Groups of 5 mice are used and compounds are dosed initially at a level of 250 mg./kg. The dose is then reduced sequentially until a minimum effective dose (MED) is found. The MED for 1-(4-chlorophenyl)-1,2,3,4-tetrahydro-2-(1,2,4-triazol-1-yl)-1-naphthol in this test was 25 mg. per kg. No overt signs of toxicity were noted even at the highest dose (250 mg./kg.).

Thus, according to a further feature of the invention there is provided a pharmaceutical or veterinary antifungal composition which comprises a compound of the formula I together with a pharmaceutically or veterinarily acceptable diluent or carrier.

The composition of the invention may be in a conventional pharmaceutical form suitable for oral administration, for example a tablet, a capsule, an emulsion or an aqueous or oily solution or suspension, or suitable for topical application, for example a cream, ointment or gel. The composition may contain conventional pharmaceutical excipients, and may be manufactured by conventional pharmaceutical techniques.

Preferred pharmaceutical or veterinary compositions of the invention are compositions suitable for oral administration, and particularly tablets or capsules.

The compounds of the invention also possess antifungal properties which are useful in combatting a wide variety of plant fungal diseases.

The compounds can move acropetally in the plant tissue, and can also be volatile enough to be active in the vapour phase against fungi on the plant.

The compounds may be used as such for fungicidal purposes but are more conveniently formulated into compositions for such usage. The invention thus provides also a plant fungicidal composition comprising a compound of general formula (I) and a non-pharmaceutical carrier or diluent.

The invention also provides a method of combatting fungal diseases in a plant, which comprises applying to the plant, to seed of the plant or to the locus of the plant or seed a compound of the formula I.

The compound can be applied in a number of ways, for example it can be formulated or unformulated, directly to the foliage of a plant, to seeds or to the medium in which plants are growing or are to be planted, or it can be sprayed on, dusted on or applied as a cream or paste formulation, or it can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged, and the choice of a suitable conventional composition, and the method by which such a composition may be manufactured, are apparent to those skilled in the art.

Thus, according to a further feature of the invention there is provided an agricultural or horticultural antifungal composition comprising a compound of the formula I as defined above, optionally with a non-pharmaceutical inert diluent or carrier.

The plant fungicidal compositions of this invention can comprise also other compound(s) having biological activity, e.g. compounds having similar or complementary fungicidal activity or compounds having plant growth regulating, herbicidal or insecticidal activity.

The invention is illustrated but not limited, by the following Examples, in which "parts" are by weight:

EXAMPLE 1

2-Bromo-6,7-dichloro-1-(4-chlorophenyl)-1,2,3,4-tetrahydro-1-naphthol (3.5 g.) and sodium 1,2,4-triazole (3.5 g.) in N,N-dimethylacetamide (15 ml.) were stirred and heated at 100° C. in an oil bath for 18 hours. The reaction mixture was poured into water and extracted with ethyl acetate (3×50 ml.), the extract was dried, and the solvent was evaporated under reduced pressure. The residual oil was chromatographed on silica (Merck's Grade 7734) using ethyl acetate as eluant, to give an oil, which crystallised on standing to give 6,7-dichloro-1-(4-chlorophenyl)-1,2,3,4-tetrahydro-1-(1,2,4-triazol-1-yl)-1-naphthol, m.p. 195°–197° C.

The 2-bromo-1-(4-chlorophenyl)-1,2,3,4-tetrahydro-1-naphthol used as the starting material in the above process may be obtained as follows:

Magnesium turnings (1.5 g.) and diethyl ether (30 ml.) were stirred while a solution of p-bromochlorobenzene (12 g.) in diethyl ether (100 ml.) was added to form the Grignard reagent. The solution was heated under reflux for 10 minutes, then a solution of 6,7-dichloro-1,2,3,4-tetrahydro-1-oxonaphthalene (9 g.) in diethyl ether (100 ml.) was added over 20 minutes, and the mixture was then heated under reflux for 30 minutes. The reaction mixture was cooled and acidified with 2N hydrochloric acid (50 ml.), and the ether layer was separated, dried, and evaporated to dryness leaving an oil. This residual oil was dissolved in toluene (300 ml.), toluene-p-sulphonic acid (0.5 g.) was added, and the solution was heated under reflux in an Dean and Stark apparatus for 2 hours, while 0.5 ml. of water was collected. The toluene was evaporated under reduced pressure and the residual oil was chromatographed on silica (Merck's Grade 7734) using petroleum ether (b.p. 60°–80° C.) as the eluant, to give 6,7-dichloro-1-(4-chlorophenyl)-3,4-dihydronaphthalene as a white crystalline solid, m.p. 106°–108° C.

6,7-Dichloro-1-(4-chlorophenyl)-3,4-dihydronaphthalene (3.0 g.) was dissolved in acetone (80 ml.), then water (30 ml.) was added, followed by a solution of N-bromoacetamide (3.0 g.) in acetone (40 ml.), and the mixture was stirred for 2 hours. The reaction mixture was then poured into water (150 ml.) and extracted with ether (3×80 ml.), the extracts were combined and dried, and the solvent was evaporated under reduced pressure to leave an oil. This residual oil was chromatographed on silica (Merck's Grade 7734), using 30% by volume of diethyl ether in petroleum ether (b.p. 60°–80° C.) as the eluant, to give the required 2-bromo-6,7-dichloro-1-(4-chlorophenyl)-1,2,3,4-tetrahydro-1-naphthol, m.p. 103°–104.5° C.

EXAMPLE 2–13

The process described in Example 1 was repeated, using the appropriate substituted starting materials to give the following compounds:

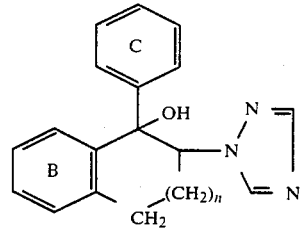

| Ex. | Substituent in ring B | Substituent in ring C | n | M.p.(°C.) |
|---|---|---|---|---|
| 2 | — | 4-chloro | 0 | 107–110 |
| 3 | — | 2,4-dichloro | 0 | 190–191.5 |
| 4 | — | 4-chloro | 1 | 195–197 |
| 5 | — | 2,4-dichloro | 1 | 227–229 |
| 6 | 6,7-dichloro | 4-fluoro | 1 | 82–89 |
| 7 | 6,7-dichloro | 2,4-dichloro | 1 | 113–120 |
| 8 | 6-chloro | 4-chloro | 1 | 229–231 |

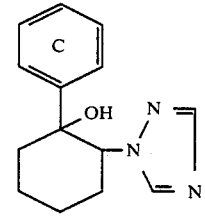

| Ex. | Substituent in ring C | M.p.(°C.) |
|---|---|---|
| 9 | — | 167–169 |
| 10 | 2,4-dichloro | 255–257 |
| 11 | 4-chloro | 181–183 |

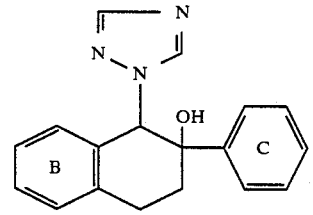

| Ex. | Substituent in ring C | M.p.(°C.) |
|---|---|---|
| 12 | 4-chloro | 208–210 |
| 13 | 2,4-dichloro | 207–210 |

EXAMPLE 14

A mixture of 5, 10, 25, 50, 100 or 250 parts of 1-(4-chlorophenyl)-1,2,3,4-tetrahydro-2-(1,2,4-triazol-1-yl)-1-naphthol with 70 parts of calcium carbonate and 200 parts of a 10% maize starch paste is dried and then passed through a 16 mesh screen. 5 parts of magnesium stearate are added and the granules are compressed to give a range of tablets suitable for oral administration for therapeutic purposes.

This active ingredient may be replaced by a therapeutically equivalent amount of any other triazole derivative as hereinbefore defined.

EXAMPLE 15

A mixture of 2, 5, 25, 50 or 100 parts of 1-(4-chlorophenyl)-1,2,3,4-tetrahydro-2-(1,2,4-triazol-1-yl)-1-naphthol, 500 parts of lactose and 100 parts of maize starch is treated with sufficient 10% maize starch paste to give a granular mass. The mixture is passed through a 16 mesh screen, dried, mixed with 8 parts of magnesium stearate and compressed into tablets, giving a range of tablets suitable for oral administration for therapeutic purposes.

The active ingredient may be replaced by a therapeutically equivalent amount of any other triazole derivative as hereinbefore defined.

EXAMPLE 16

A mixture of 10 parts of 1-(4-chlorophenyl)-1,2,3,4-tetrahydro-2-(1,2,4-triazol-1-yl)-1-naphthol and 190 parts of wheat germ oil is filled into soft gelatine capsules, to give capsules suitable for oral administration for therapeutic purposes.

The active ingredient may be replaced by a therapeutically equivalent amount of any other triazole derivative as hereinbefore defined.

EXAMPLE 17

A solution of 10 parts of 1-(4-chlorophenyl)1,2,3,4-tetrahydro-2-(1,2,4-triazol-1-yl)-1-naphthol in 83 parts of water, 250 parts of glycerol and 125 parts of ethyl alcohol is mixed with a solution of 300 parts of sucrose in 150 parts of water. A suitable flavouring agent and colouring matter are then added to produce a syrup suitable for oral administration for therapeutic purposes.

The active ingredient may be replaced by a therapeutically equivalent amount of any other triazole derivative as hereinbefore defined.

EXAMPLE 18

A mixture of 3 parts of gum acacia and 1.5 parts of gum tragacanth is added to a mixture of 1 part of 1-(4-chlorophenyl)-1,2,3,4-tetrahydro-1-(1,2,4-triazol-1-yl)-1-naphthol and 33.7 parts of liquid paraffin. To the thoroughly triturated mixture is added slowly with stirring a solution of 0.1 part of cetyl alcohol-polyoxyethylene condensate, 40 parts of sucrose, 0.03 part of propyl p-hydroxybenzoate, 0.3 parts of methyl p-hydroxybenzoate, a suitable flavouring agent and 0.002 part of edible dyestuff in 110 parts of water. The mixture is then homogenized in conventional manner known in the art to produce an emulsion suitable for oral administration for therapeutic purposes.

The active ingredient may be replaced by a therapeutically equivalent amount of other triazole derivative as hereinbefore defined.

EXAMPLE 19

A mixture of 0.5 part of finely divided 1-(4-chlorophenyl)-1,2,3,4-tetrahydro-2-(1,2,4-triazol-1-yl)-1-naphthol in 3 parts of propylene glycol and 2 parts of ethylene glycol monoethyl ether was added to a stirred mixture of 4 parts of lanolin and 90.5 parts of molten soft white paraffin. The resulting mixture was allowed to cool to room temperature with rapid stirring, to give a uniform ointment containing 0.5% by weight of active ingredient suitable for topical administration for therapeutic purposes.

The active ingredient may be replaced by another triazole derivative as hereinbefore defined to give similar ointments.

EXAMPLE 20

A solution was prepared of 1 part of 1-(4-chlorophenyl)-1,2,3,4-tetrahydro-2-(1,2,4-triazol-1-yl)-1-naphthol in 20 parts of ethanol and 27 parts of diethylene glycol monoethyl ether, then 50 parts of purified water was added, followed by 2 parts of a carboxypolymethylene gelling agent ("Carbapol 940"-trade mark) to give a finely dispersed gel suitable for topical administration for therapeutic purposes.

The active ingredient may be replaced by any other triazole derivative as hereinbefore described.

EXAMPLES 21–27

The process described in Example 1 was repeated, using the appropriate α-bromo-alcohol as starting material, to manufacture the following compounds:

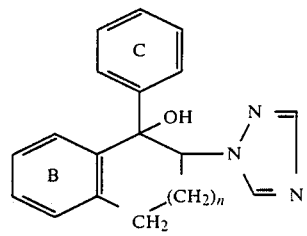

| Ex. | Substituent in ring B | Substituent in ring C | n | M.p.(°C.) |
|---|---|---|---|---|
| 21 | 5-chloro | 2,4-dichloro | 1 | glass |
| 22 | 6-chloro | 2,4-dichloro | 1 | glass |
| 23 | 6-chloro | — | 1 | 197–200 |
| 24 | 5-chloro | 4-chloro | 1 | glass |
| 25 | 6-fluoro | 4-chloro | 1 | 191–193 |
| 26 | 6-fluoro | 2,4-dichloro | 1 | glass |

The compounds indicated as "glasses" in the above table were fully characterised, and their structures confirmed, by nuclear magnetic resonance (n.m.r.) spectroscopy.

What we claim is:

1. An alicyclic alcohol compound of the formula:

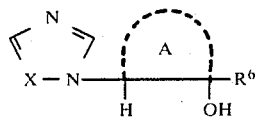

wherein $R^6$ is an unsubstituted phenyl radical or a phenyl radical bearing 1 to 5 substituents selected from halogen atoms, amino, nitro, cyano, phenyl and halogenophenyl radicals, and alkyl, halogenoalkyl, alkoxy, halogenoalkoxy, alkylthio, alkylenedioxy, alkylamino and dialkylamino radicals wherein each alkyl, alkoxy or alkylene part is of 1 to 10 carbon atoms, X is a nitrilo or methine radical, and the ring A is an indane, tetrahydronaphthalene or benzocycloheptane ring each of which is either unsubstituted or is substituted in the benzene ring thereof with 1 to 4 substitutents as defined above.

2. A compound as claimed in claim 1 wherein $R^6$ is a phenyl, 2-, 3- or 4-chlorophenyl, 2-, 3- or 4-fluorophenyl, 2-, 3- or 4-bromophenyl, 2,3-, 2,4-, 2,5-, 2,6-, 3,4- or 3,5-dichlorophenyl, 2,3-, 2,4-, 2,5-, 2,6-, 3,4- or 3,5-difluorophenyl, 2-chloro-4-fluorophenyl, 4-chloro-2-fluorophenyl, 2-bromo-4-chlorophenyl, 4-bromo-2-chlorophenyl radical, or a phenyl radical which is substituted by one or two substituents selected from amino, nitro, cyano, methyl, ethyl, propyl, butyl, pentyl, hexyl, heptyl, octyl, nonyl, decyl, chloromethyl, dichloromethyl, trichloromethyl, fluoromethyl, difluoromethyl, trifluoromethyl, 2,2,2-trichloroethyl, 2,2,2-trifluoroethyl, methylthio, ethylthio, propylthio, hexylthio, decylthio, methylenedioxy, ethylidenedioxy, 1-methylethylidenedioxy, 1,2-ethylenedioxy, 1,2-propylenedioxy, 1-methyl-1,2-propylenedioxy, 1,2-butylenedioxy, 1-methyl-1,2-butylenedioxy, 1-ethyl-1,2-butylenedioxy, methoxy, ethoxy, propoxy, hexyloxy, decyloxy, chloromethoxy, trichloromethoxy, fluoromethoxy, 2,2,2-trichloroethoxy, methylamino, ethylamino, propylamino, hexylamino, decylamino, dimethylamino, diethylamino, ethylmethylamino, dopropylamino, dihexylamino and didecylamino radicals, X is a nitrilo radical and A is a indane, 4-, 5-, 6- or 7-fluoroindane, 4,5-, 5,6-, 6,7-, 4,6-, 4,7- or 5,7-dichloroindane, 4,5-, 5,6-, 6,7-, 4,6-, 4,7- or 5,7-difluoroindane, 1,2,3,4-tetrahydronaphthalene, 5-, 6-, 7- or 8-chloro-1,2,3,4-tetrahydronaphthalene, 5-, 6-, 7- or 8-fluoro-1,2,3,4-tetrahydronaphthalene, 5,6-, 5,7-, 5,8-, 6,7-, 6,8- or 7,8-dichloro-1,2,3,4-tetrahydronaphthalene and or 5,6-, 5,7-, 5,8-, 6,7-, 6,8- or 7,8-difluoro-1,2,3,4-tetrahydronaphthalene ring.

3. A compound as claimed in claim 1 wherein $R^6$ is a phenyl radical or a phenyl radical bearing one or two halogen substituents, X is a nitrilo radical, and A is an optionally substituted indane or 1,2,3,4-tetrahydronaphthalene ring as defined in claim 1.

4. A compound as claimed in claim 3 wherein $R^6$ is a phenyl, 4-chloro-, 4-fluoro-, 2,4-dichloro- or 2,4-difluoro-phenyl radical, X is a nitrilo radical, and A is an, indane, 5-chloro, 6-chloro-, 6,7-dichloro or 6-fluoro-1,2,3,4-tetrahydronaphthalene ring.

5. A compound as claimed in claim 4 wherein the hydroxy and $R^6$ substituents are on C-1 of said tetrahydronaphthalene or said substituted tetrahydronaphthalene ring.

6. A compound as claimed in claim 5 which is 1-(4-chlorophenyl)-1,2,3,4-tetrahydro-2-(1,2,4-triazol-1-yl)-1-naphthol or 6-chloro-1-(4-chlorophenyl)-1,2,3,4-tetrahydro-1-(1,2,4-triazol-1-yl)-1-naphthol.

7. A pharmaceutical or veterinary antifungal composition which comprises a fungicidally effective amount of a compound as claimed in claim 1 together with a pharmaceutically or veterinary acceptable diluent or carrier.

8. An agricultural or horticultural antifungal composition comprising a fungicidally effective amount of a compound as claimed in claim 1, together with a non-pharmaceutical inert diluent or carrier.

9. A method of combatting fungal diseases in a plant, which comprises applying to the plant, to seed of the plant or to the locus of the plant or sead a fungicidally effective amount of a compound as claimed in claim 1, or a composition as claimed in claim 9.

10. A method of combatting a fungal disease in an animal requiring such treatment which comprises administering to said animal a fungicidally effective amount of a compound as claimed in claim 1.

* * * * *